US009345881B2

(12) United States Patent
Lineaweaver

(10) Patent No.: US 9,345,881 B2
(45) Date of Patent: May 24, 2016

(54) GENETIC ALGORITHM BASED AUDITORY TRAINING

(71) Applicant: Sean Lineaweaver, Gig Harbor, WA (US)

(72) Inventor: Sean Lineaweaver, Gig Harbor, WA (US)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/684,710

(22) Filed: Apr. 13, 2015

(65) Prior Publication Data

US 2015/0209585 A1   Jul. 30, 2015

Related U.S. Application Data

(62) Division of application No. 13/774,377, filed on Feb. 22, 2013, now Pat. No. 9,031,663.

(51) Int. Cl.
*A61N 1/36* (2006.01)
*G06F 19/00* (2011.01)
*G06N 3/12* (2006.01)
*H04R 25/00* (2006.01)
*A61B 5/12* (2006.01)
*A61N 1/05* (2006.01)
*A61N 1/372* (2006.01)

(52) U.S. Cl.
CPC .......... *A61N 1/36032* (2013.01); *G06F 19/345* (2013.01); *G06F 19/3481* (2013.01); *G06N 3/126* (2013.01); *H04R 25/70* (2013.01); *A61B 5/12* (2013.01); *A61B 5/123* (2013.01); *A61N 1/0541* (2013.01); *A61N 1/37241* (2013.01); *A61N 1/37247* (2013.01); *G06F 19/3406* (2013.01); *H04R 2225/41* (2013.01); *H04R 2225/43* (2013.01)

(58) Field of Classification Search
CPC ............ A61N 1/36032; A61N 1/0541; A61N 1/37235; A61N 1/37264
See application file for complete search history.

(56) References Cited

U.S. PATENT DOCUMENTS

| | | | |
|---|---|---|---|
| 6,879,860 | B2 | 4/2005 | Wakefield et al. |
| 8,301,259 | B2 | 10/2012 | Wakefield et al. |
| 2010/0152813 | A1 | 6/2010 | Lineaweaver et al. |
| 2010/0280307 | A1 | 11/2010 | Lineaweaver et al. |
| 2011/0060383 | A1 | 3/2011 | Lineaweaver et al. |
| 2011/0060702 | A1* | 3/2011 | Lineaweaver ................. 706/11 |

OTHER PUBLICATIONS

Lineaweaver, et al., "Psychometric Augmentation of an Interactive Genetic Algorithm for Optimizing Cochlear Implant Programs," 13th Annual Genetic and Evolutionary Computation Conference, GECCO 2011, Proceedings, Dublin, Ireland, Jul. 12-16, 2011, pp. 1755-1762.

* cited by examiner

*Primary Examiner* — Rex R Holmes
(74) *Attorney, Agent, or Firm* — Edell, Shapiro & Finnan, LLC

(57) ABSTRACT

Embodiments of the present invention are generally directed to the use of a genetic algorithm for the purpose of providing progressive and adaptive auditory training (rehabilitation) to a recipient of a hearing prosthesis. In general, the genetic algorithm is used to adapt the training process to automatically increase the difficulty of the training based on recipient feedback and performance. That is, the genetic algorithm progressively removes perceivable sounds from the training process so as to generate groups of sounds that are difficult for a recipient to perceive.

20 Claims, 10 Drawing Sheets

FIG. 2

AUDITORY TRAINING LIBRARY
200

| REPRESENTATIVE BIT STRING | SOUND TOKEN | |
|---|---|---|
| 1 1 1 ... 0 0 0 | u | } 202 |
| 1 0 1 ... 0 0 1 | e | } 204 |
| 1 1 0 ... 1 0 0 | i | } 206 |
| 0 0 0 ... 0 1 0 | y | } 208 |
| 1 0 0 ... 1 0 1 | r | } 210 |
| 0 1 1 ... 1 0 1 | m | } 212 |
| 0 1 0 ... 0 0 1 | /p | } 214 |
| 0 1 0 ... 1 1 1 | /b/ | } 216 |
| 1 1 1 ... 1 0 1 | aba | } 218 |
| 0 1 1 ... 1 1 1 | aga | } 220 |
| 0 0 1 ... 0 1 0 | ec | } 222 |
| 0 0 0 ... 1 1 0 | oc | } 224 |
| 0 1 1 ... 1 1 0 | Cat | } 226 |
| 1 1 0 ... 0 1 0 | Kit | } 228 |
| 0 1 1 ... 0 1 1 | Ball | } 230 |

FIG. 7A

USER INTERFACE 570 — PLEASE SELECT ONE OF THE FOLLOWING CHOICES.

1. THE FIRST TONE WAS HIGHER THAN THE SECOND TONE.

2. THE SECOND TONE WAS HIGHER THAN THE FIRST TONE.

3. THE FIRST AND SECOND TONES WERE THE SAME.

4. ONLY ONE TONE WAS PLAYED.

5. REPLAY SOUND

GENETIC ALGORITHM BASED AUDITORY TRAINING

CROSS-REFERENCE TO RELATED APPLICATIONS

The present application is a divisional application of U.S. Provisional Patent Application Ser. No. 13/774,377, filed on Feb. 22, 2013, now issued as U.S. Pat. No. 9,031,663, the content of which is hereby incorporated by reference herein.

BACKGROUND

1. Field of the Invention

The present invention relates generally to auditory training, and more particularly, to genetic algorithm based auditory training.

2. Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Several types of hearing prosthesis have been developed to treat conductive hearing loss by generating mechanical motion of a recipient's cochlea fluid. These hearing prostheses may include, for example, acoustic hearing aids, bone conduction devices, implantable mechanical stimulators, etc. The selection of a specific type of hearing prosthesis for use by a recipient may be based on the recipient's degree of residual hearing, age, or other factors.

Those suffering from certain forms of sensorineural hearing loss are unable to derive suitable benefit from hearing prostheses that generate mechanical motion of the cochlea fluid. However, such individuals may benefit from hearing prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem implants may also be proposed when a recipient experiences sensorineural hearing loss resulting from damage to the auditory nerve, which forwards signals from the cochlea to the brain.

When hearing prostheses are first used by a recipient, nerve pulses will occur in the recipient's auditory nerve and brain causing a hearing sensation. However, certain recipients may have difficulty interpreting these nerve pulses and do not correctly perceive the sound. As such, recipients of hearing prostheses typically receive some form of auditory training that, over time, enables the recipients to discriminate between different sounds and to attach meaning to those sounds.

SUMMARY

In one aspect of the invention, a method is provided. The method comprises selecting an initial set of auditory training sound tokens from an auditory training library, presenting the initial set of sound tokens to a recipient via a hearing prosthesis, receiving recipient feedback in response to the presented sound tokens, wherein the feedback indicates the recipient's perception of the sound tokens, and executing a genetic algorithm based on the recipient's perception of the sound tokens to create a second set of auditory sound tokens for presentation to the recipient.

In another aspect of the present invention, a method is provided. The method comprises selecting a set of parameter values for a cochlear implant, providing the set of parameter values to the cochlear implant for use in delivering stimulation to a recipient, and executing a genetic algorithm based auditory training process in which sound tokens are processed and delivered to the recipient in accordance with the set of parameter values.

BRIEF DESCRIPTION OF THE DRAWINGS

Embodiments of the present invention are described herein in conjunction with the accompanying drawings, in which:

FIG. 2 is a schematic diagram of an auditory training library in accordance with embodiments of the present invention;

FIGS. 6A-7B illustrate example display screens that may be provided to a recipient during auditory training in accordance with embodiments of the present invention.

DETAILED DESCRIPTION

Embodiments of the present invention are generally directed to the use of a genetic algorithm (GA) for the purpose of providing progressive and adaptive auditory training (rehabilitation) to a recipient of a hearing prosthesis. In general, the genetic algorithm is an interactive augmented genetic algorithm (IAGA) that is used to adapt the training process to automatically increase the difficulty of the training based on recipient feedback and performance. That is, the IAGA progressively removes perceivable sounds from the training process so as to generate groups of sounds that are difficult for a recipient to perceive.

A standard or traditional genetic algorithm is, in general, an adaptive procedure that implements aspects of biological evolution including, for example, "natural selection," "procreation with inheritance," and "random mutation," among others. The underlying premise of a traditional genetic algorithm is that the evolutionary process will, over multiple generations, produce an optimal "organism."

Genetic algorithms are capable of evolving surprisingly complex and interesting structures. Such structures may represent not only solutions to problems, but also strategies for playing games, visual images, or even simple computer programs. The Darwinian theory of evolution depicts biological systems as the product of the ongoing process of natural selection. Likewise, genetic algorithms allow the utilization of computing devices to evolve solutions over time, instead of designing them by hand. Because almost any method, theory, or technique can be programmed on a computing device, this implies an approach to problem solving that can be, at least partially, automated by a computer.

Hearing prostheses may include, for example, acoustic hearing aids, bone conduction devices, mechanical stimulators, auditory brain stimulators cochlear implants, mixed-mode devices, etc. It is to be appreciated that genetic algorithm based auditory training in accordance with embodiments of the present invention may be used in connection with any of the above or other hearing prostheses. However, merely for ease of description, embodiments of the genetic algorithm based auditory training are primarily described herein in connection with one exemplary hearing prosthesis, namely a cochlear implant (also commonly referred to as cochlear implant device, cochlear prosthesis, and the like; simply "cochlear implant" herein).

Figure 1:
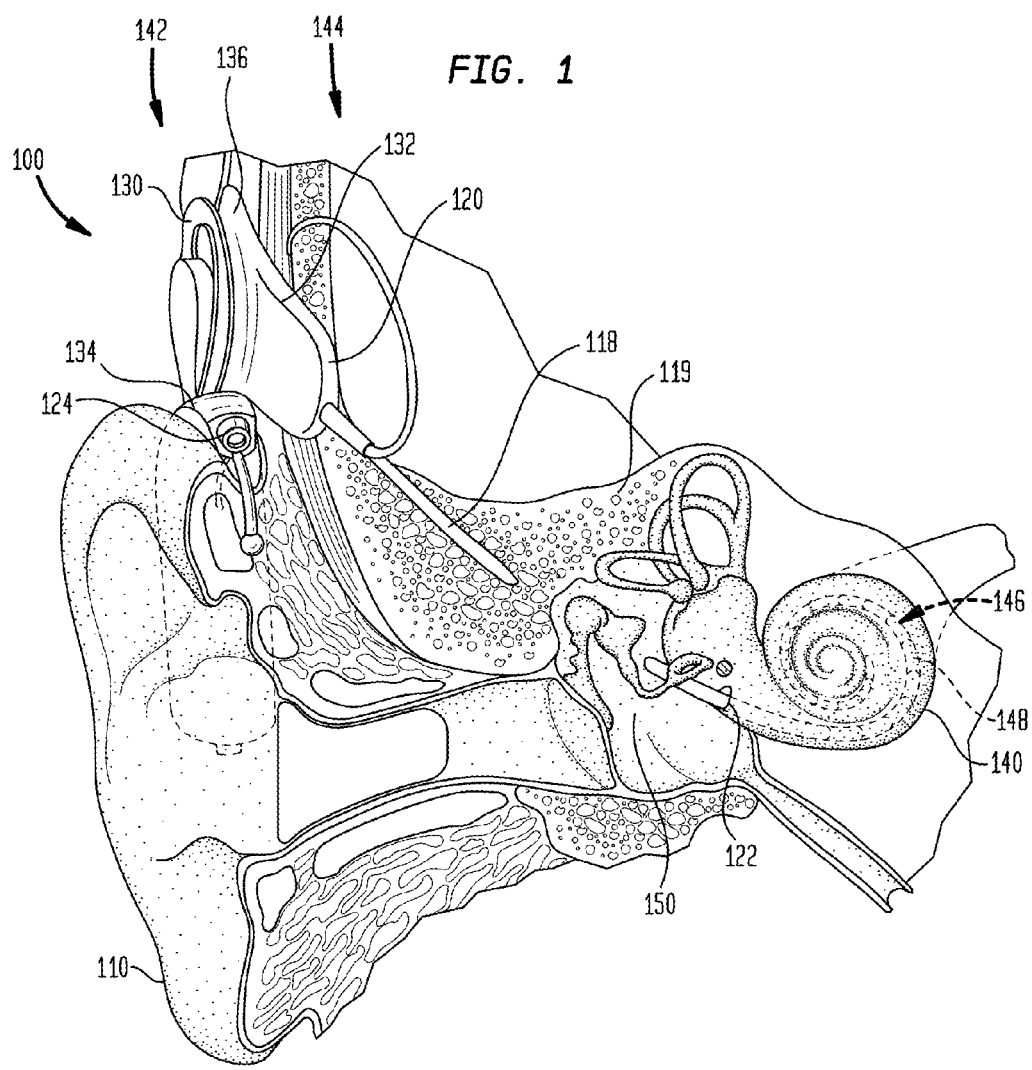
FIG. 1 is a schematic diagram of a cochlear implant that may be used in conjunction with embodiments of the present invention.

FIG. 1 is perspective view of an exemplary cochlear implant 100 that may be used in conjunction with genetic algorithm based auditory training in accordance with embodiments of the present invention. Cochlear implant 100 comprises an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 126, a power source (not shown), an external coil 130 and, generally, a magnet (not shown) fixed relative to the external coil 130. The sound processor 126 processes electrical signals generated by a sound input element 124 that is positioned, in the depicted embodiment, by auricle 110 of the recipient. The sound processor 126 provides the processed signals to external coil 130 via a cable (not shown).

The internal component 144 comprises an elongate stimulating assembly 118, a stimulator unit 120, and an internal receiver/transceiver unit 132, sometimes referred to herein as transceiver unit 132. The transceiver unit 132 is connected to an internal coil 136 and, generally, a magnet (not shown) fixed relative to the internal coil 136. Internal transceiver unit 132 and stimulator unit 120 are sometimes collectively referred to herein as a stimulator/transceiver unit.

The magnets in the external component 142 and internal component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 has a proximal end connected to the stimulator unit 120 and a distal end implanted in cochlea 140 through the use of the implantation imaging techniques presented herein. Elongate stimulating assembly 118 also includes a contact array 146 that comprises a plurality of stimulating contacts 148 that may be electrical and/or optical contacts. Stimulating assembly 118 extends from stimulator unit 120 to cochlea 140 through mastoid bone 119 and a cochleostomy 122.

As noted, a genetic algorithm is an adaptive procedure that implements aspects of evolution that, through multiple iterations, produces an organism that is best suited for its environment. An iteration of a genetic algorithm begins with a generation of organisms ("parents") that are used to produce a succeeding generation of organisms ("children"). This typically involves two steps, namely selection and procreation. Selection involves the choosing of a subset of organisms as the potential parents of the organisms of the succeeding generation (the children). Procreation involves the creation of children from the selected sets of potential parents.

Traditionally, binary strings of zeros (0s) and ones (1s) have been used to represent organisms within a genetic algorithm (both parents and children). Merely for ease of illustration, traditional binary bit strings will also be used herein to represent organisms. However, as described further below, other encodings are also possible and may be used in alternative embodiments of the present invention. For example, other variations organisms are: lists of numbers indexed into an instruction table, nodes in a linked list, hashes, objects, etc.

The basic idea of the genetic algorithm is that first a population of organisms is created in a computing device (typically with genes stored as binary strings in the device's memory), and then the population is evolved with use of the principles of variation, selection, and inheritance. That is, selection operates on strings of binary digits stored in the memory of a computing device, and over time, the functionality of these strings evolves in much the same way that the deoxyribonucleic acid (DNA) of species naturally evolve. There are many ways of implementing a genetic algorithm, but the most basic is that suggested by J. H. Holland, in Adaptation in Natural and Artificial Systems, Univ. of Michigan Press, Ann Arbor, Mich., 1975, reprinted by MIT Press, Cambridge, Mass., 1992, which is hereby incorporated by reference herein.

In order to execute the selection process of a genetic algorithm, each organism in a generation is first assigned a fitness value through execution of a fitness function. On the basis of these fitness values, the selection function evaluates the organisms. After selection, genetic operators are applied probabilistically. For example, some organisms may have bits in their genes mutated from a 1 to a 0 or a 0 to a 1, and/or parts of different organisms' genes may then be combined into new ones. The resulting population comprises the next generation and the process repeats itself.

The fitness function is the primary place in which a genetic algorithm is tailored to a specific problem. Once all organisms in the population of a particular generation have been evaluated, their fitness values are used as the basis for selection. Selection is implemented by eliminating low-fitness individuals from the population, and inheritance is often implemented by passing on characteristics of high-fitness individuals to subsequent ones. Genetic operators such as mutation (flipping individual bits) and crossover or inheritance (exchanging sub-strings of two organisms to obtain two offspring) are applied probabilistically to the selected individuals to produce new organisms. By replacing members of the old generation with such new organisms, new generations are produced so that the old generation is completely replaced ("synchronously"), or so that the new and old members of the generation overlap ("asynchronously"). The genetic operators have been shown to generate new organisms that, on average, are better than the average fitness of their parent organisms. Therefore, when this cycle of evaluation, selection, and genetic operations is iterated for many generations, the overall fitness of the population generally improves, on average, and the organisms represent improved "solutions" to the specific problem.

Selection and reproduction can be performed in any of several ways. For example, the least fit organisms may be arbitrarily eliminated from the population while copies of all the remaining organisms are made. Alternatively, organisms may be replicated in direct proportion to their fitness or the fitness of the organisms may be scaled in any of several ways such that organisms are replicated in direct proportion to their scaled values. Likewise, the crossover operator can pass on both offspring to the new generation, or it can arbitrarily choose one to be passed on.

As noted, embodiments presented herein are directed to using a modified genetic algorithm, referred to herein as an interactive augmented genetic algorithm (IAGA), during auditory training of a recipient of a cochlear implant or other hearing prosthesis. Specifically, embodiments may be directed to executing an IAGA to select sounds for delivery to the recipient during the training process in order to improve the recipient's sound perception. In essence, the IAGA is used to adapt the auditory training to filter out sounds that are easily perceived by a user and such that to automatically increase the difficulty of the training process based on the recipient's feedback.

For example, if it is determined that the auditory training is too easy for the recipient, the difficulty of the auditory training may be increased by, for example, reducing the signal to noise ratio, adding additional noise sources (e.g., in the case of music, adding more instruments), and increasing the difficulty of a listening discrimination task (e.g., moving from an obvious phoneme confusion such as 'k' vs. 's' to a more subtle one of 'r' vs. 'l'). In practice, these changes may be gradual and occur through the implementation of the genetic algorithm (i.e., the genetic algorithm is used to progressively and adaptively increase the difficulty of the auditory training).

As described further below, genetic algorithms used in accordance with embodiments of the present invention may be IAGAs. An IAGA is a modified version of an interactive genetic algorithm (IGA) that explicitly incorporates human feedback into the evolutionary process of the genetic algorithm. An IAGA uses modifications to the standard genetic algorithm and/or IGA that are more consistent with psychometric theory and practice. These modifications implemented in an IAGA may include, for example, representation, generation, selection, crossover, mutation, stopping criteria, and initialization.

In one embodiment, the genetic algorithm operates to generate successive generations of multiple groups of sounds for delivery to the recipient. Recipient feedback during execution of such a genetic algorithm forms a basis for selecting sounds in each of the successive generations. In other words, selection is based on the perceptual auditory judgment of the recipient during execution of the genetic algorithm. In each generation, less than all (for example, half) of the groups of sounds are selected and used to determine a larger number of groups of sounds for the next generation (e.g., twice as large, if it is desired that all generations be of the same size).

In embodiments, each organism of the auditory training genetic algorithm corresponds to a sound file or recording (collectively referred to as sound tokens) that may be played to a recipient through the cochlear implant. Embodiments of the present invention may make use of a large number of different types of sound tokens during auditory training. The collection of possible sound tokens is referred to herein as an auditory training library.

In certain embodiments, the auditory training library includes sound tokens comprised of language/speech sounds such as consonant sounds formed based using different phonetic attributes including manner (e.g., stop, fricative, affricate, nasal, liquid, glide), place (e.g., bilabial, labiodental, linguadental, linguaalveolar, linguapalatal, linguavelar, glottal), voice (e.g., voiced or voiceless); vowels (e.g., monophthongs or diphthongs), words, morphemes, and/or other formants or phonemes. The sound tokens may be further defined by combinations of speech characteristics. In further embodiments, sound tokens may comprise parts of music (e.g., instruments, musical notes, pitches, lyrics, etc.) or tones. In certain embodiments described further below, the auditory training library includes recipient-specific sound tokens (e.g., a baby's cry, a spouse's voice, etc.) It is to be appreciated that the above sound tokens are merely exemplary and that a large number of different types of sounds may be used during auditory training.

Each organism (sound token) in the auditory training library is represented by a set of $N_b$ "genes" (bits) such that the number of possible unique organisms is $2^{Nb}$. In other words, each sound token in the auditory training library is mapped to a unique binary bit string that is used for the mathematical operations. FIG. 2 is a schematic diagram illustrating a subset of an auditory training library 200. FIG. 2 illustrates fifteen (15) different sound tokens 202-230 and a portion of their corresponding representative bit strings. For ease of description herein, sound tokens and their corresponding bit strings will be referred to using the same reference numbers.

It is to be appreciated that a large number of sound tokens may require the use of a large number of distinct bit streams. As such, the bit streams used in embodiments of the present invention may have different lengths that depend on the number of sound tokens within the auditory training library. Merely for ease of illustration, only a portion of each bit string is shown in FIG. 2.

In certain embodiments, sound tokens may be randomly mapped to bit strings. However, in other embodiments, the sound tokens are mapped to bit strings in a manner that represents similarity between sounds. For example, two sounds that sound similar may be mapped to sequential bit strings.

It is to be appreciated that the use of binary bits to represent the sound tokens is merely for ease of illustration and that encodings are also possible and may be used in alternative embodiments of the present invention. Further details of one such alternative encoding (i.e., an alternative sound token representation) are provided below.

Figure 3:
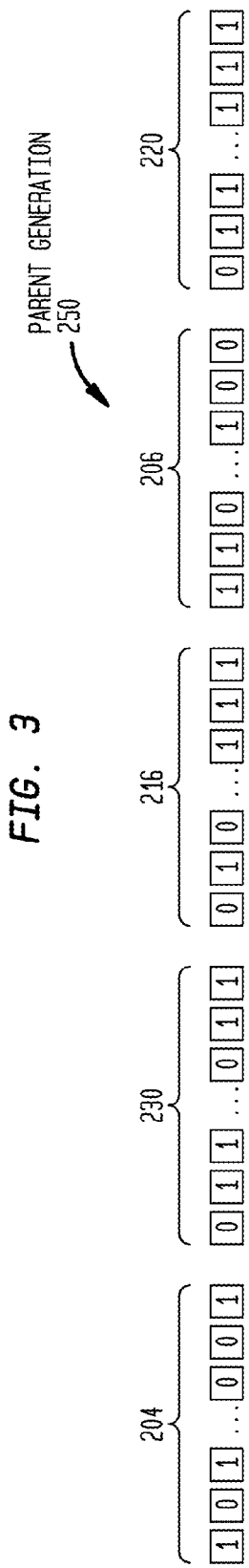
FIG. 3 is a schematic diagram of an initial generation of sound tokens for delivery to a recipient in accordance with embodiments of the present invention.

At the beginning of the genetic algorithm based auditory training, an initial set of sound tokens are selected as the parent generation of organisms for delivery to the recipient. FIG. 3 is schematic diagram of one such example initial parent generation 250. In the embodiment of FIG. 3, the parent generation 250 is comprised of five (5) organisms 204, 230, 216, 206, and 220 selected from the auditory training library 200. As noted, each organism represents a sound that may be delivered to the recipient via the recipient's cochlear implant. It is to be appreciated that the number of organisms as well as the specific organisms selected in FIG. 3 are merely illustrative and that different types and numbers of organisms may be used in alternative embodiments. The selection of the initial sound tokens may be random or based on preferences of the recipient, audiologists/clinicians, or may be selected from the results of a previous execution of the auditory training process.

As noted, a fitness function is executed to evaluate each of the organisms in each generation of a genetic algorithm. The fitness function identifies which organisms will survive to become parents and procreate, and which of the organisms will die. Generally, the number of survivors is constant from generation to generation, although that need not be the case.

In accordance with embodiments presented herein, the fitness function uses subjective feedback from the recipient. For example, a first one of the sound tokens (organisms), such as sound token 204, is presented through the cochlear implant. The recipient is then asked to identify the presented sound token 204 and the recipient's response is received and stored. This process continues until all, or a selected number, of the sound tokens in parent generation 250 have been presented to the recipient and corresponding recipient responses have been received.

For sound tokens that are accurately identified by the recipient, it is determined that the recipient may need little or no further training on that sound token (or similar tokens). However, if the recipient fails to accurately identify a sound token, it is determined that the sound token is difficult for the recipient to perceive (comprehend) and that further training on that sound token (or similar tokens) is desirable. As such, in the context of the auditory training genetic algorithm, the fitness function is based on whether or not the recipient correctly perceives a presented sound token. Sound tokens that are correctly perceived are determined to be "unfit" (i.e., selected to die), while sound tokens that are incorrectly perceived are selected to be "fit" (i.e., selected to procreate).

The concept of generally eliminating understood sound tokens and selecting misunderstood sound tokens seems, as first, counterintuitive when viewed in the context of conventional genetic algorithms. However, it is important to understand that the ultimate goal of the techniques presented herein are to improve the recipient's sound perception (i.e., to teach the recipient to hear better with the cochlear implant). As such, the IAGA is used as a tool in this regard to adaptively and progressively select sound tokens that challenge the user. Simultaneously, the IAGA substantially filters out sound tokens that are determined to be understood by the user.

It is to be appreciated that the IAGA may not permanently eliminate all understood sound tokens from subsequent generations. For example, in embodiments certain understood sound tokens may be re-presented to the recipient in a subsequent generation as a mechanism to ensure that the recipient understands that token (i.e., a double check of certain tokens may be performed).

Figure 4:
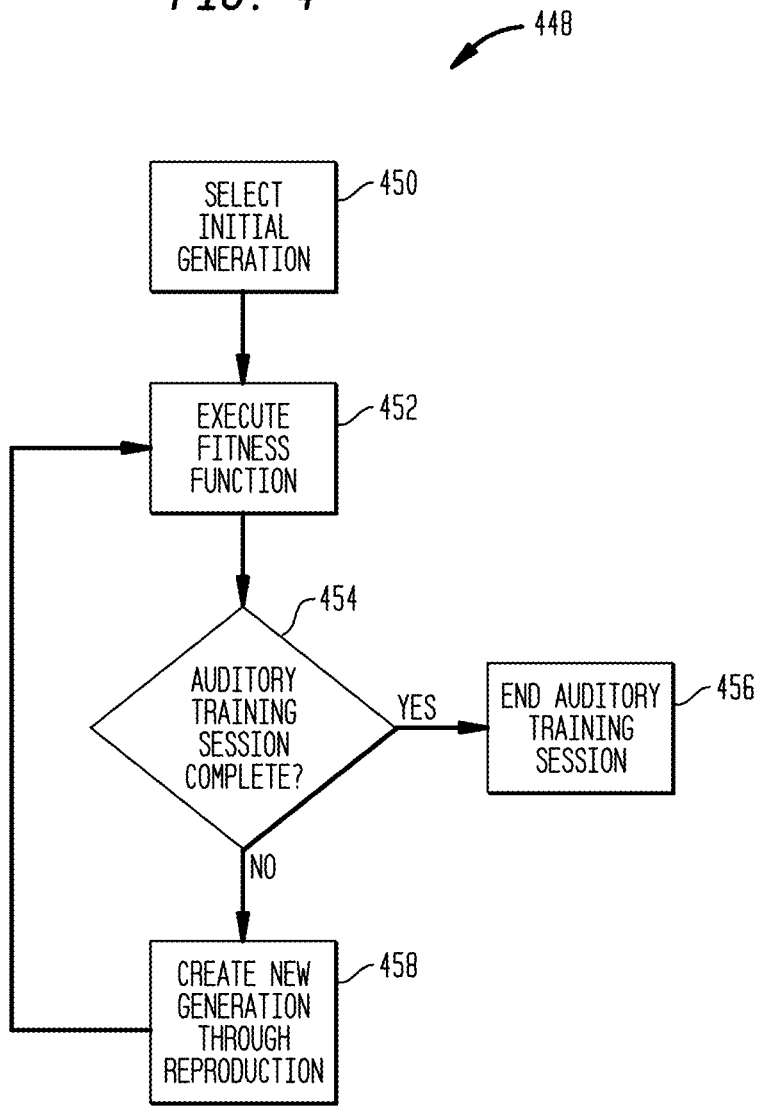
FIG. 4 is a flowchart of an auditory training method in accordance with embodiments of the present invention.

FIG. 4 is a flow chart of a genetic algorithm based auditory training method 448 in accordance with embodiments of the present invention. Additionally, merely for ease of illustration, FIG. 4 does not illustrate some of the enhancements described herein. It should be understood that the omission of enhancements in this example is merely for simplification, and other embodiments may employ each (or a subset of) the enhancements described elsewhere herein.

Method 448 of FIG. 4 begins at block 450 where an initial generation of eight sound tokens is selected. The selection of this initial generation may be performed in a number of different manners. In one embodiment, the initial sound tokens are selected at random from an auditory training library. In another embodiment, the auditory training session may be specifically directed to a specific purpose and the initial sound tokens are selected from only a subset if the auditory training library. For example, the auditory training session may be specifically directed to musical training and the initial sound tokens are all musical notes, pitches, lyrics, etc.

In one embodiment, diversity within the initial population is desired. Diversity may be defined as the average Hamming distance between the various sound tokens and ranges between 0 and 1, where a 1 indicates maximum diversity and a 0 indicates minimum diversity. If the diversity is below a threshold (e.g., 0.53), then the initial generation is determined to have an insufficient diversity and a new set of sound tokens may be selected. In certain embodiments, pre-selected sound tokens may also be included among the initial generation. These pre-selected sound tokens may be drawn from prior runs of the auditory training procedure, sound tokens from a recipient specific database of sound tokens (e.g., recipient specific or recipient added sound tokens) or sound tokens selected by a clinician based on experience, suggestions and recommendations from others, etc. The pre-selected sound tokens and/or the auditory training library may, for example, be stored in memory internal or external to an auditory training system, such as a training described in greater detail below.

Next, at block 452 a fitness function is executed on the initial generation. That is, the initial eight sound tokens are sequentially played to the recipient through the cochlear implant (e.g., via a dedicated connection or indirectly over speakers). As described above, after each sound token is played, the recipient is asked to identify the sound token. In one embodiment, the auditory training is performed by, or in the presence of, a clinician who receives the recipient's identification of the sound token. The clinician may provide the recipient with several visual choices (e.g., in a book, on a screen of a computing device, etc.) and the recipient is instructed to select which possible choice is closest to the sound that he/she perceived. In another embodiment, the auditory training is performed by the recipient on a computing device at a remote location (i.e., outside of a clinician's office). In such embodiments, the computing device is configured to visually display several choices and the user selects which possible choice is closest to the sound that he/she perceived.

After execution of the fitness function for all or a selected number of sound tokens in the initial generation, a determination is made at block 454 as to whether the genetic algorithm (and the auditory training) should be stopped (i.e., whether stopping criteria have been satisfied). In one embodiment, the auditory training is stopped after a predetermined number of generations. In another embodiment, the auditory training is stopped after a predetermined period of time.

If the stopping criteria are satisfied, then the auditory training ends at block 456. Otherwise, at block 458, a new generation is created through reproduction as described elsewhere herein. The reproduction occurs using primarily or only those sound tokens that the recipient failed to correctly identify.

After creation of the new generation, the fitness function is again executed at block 452. The process of blocks 452, 454, and 458 continue iteratively until the stopping criteria are satisfied.

The method of the above-discussed embodiment has the advantage that it can be automated, requiring little or no supervision by the clinician. It may also be repeated periodically as desired by the recipient to enhance speech perception. Separate optimizations may be performed for specific classes of input signals (e.g., speech in quiet, speech in noise, music, etc.).

As noted above, the genetic algorithm used to progressively adapt the auditory training process may be an IAGA. In general, an IAGA modifies both the procedural and algorithmic components of an IGA to better match the human-selection process. IGAs explicitly incorporate human feedback into the evolutionary process of the genetic algorithm. In its simplest form, the IGA uses a subjective recipient-generated "goodness" response in place of some objective function. Based on these responses, the population is evolved using modifications to a standard (traditional) genetic algorithm.

These modifications to the standard genetic algorithm result in a framework that is more consistent with psychometric theory and practice. Specially, modifications with respect to representation, generation, selection, crossover, mutation, stopping criteria and initialization are introduced. These modifications define the IAGA.

At the core of the IGA is a measure of the human preference. Psychometric techniques for obtaining such preference judgments (e.g., scaling or ranking) impose certain limits on general properties of an IGA. From the standpoint of memory load, the number of stimuli a recipient can judge at any one time is typically bounded by the "7±1" rule. While it is possible to exceed this bound, in practice, the clinician should provide some means for the participant to compare among options as part of the response procedure. From the standpoint of task load, recipients often fatigue after 1-2 hours of testing, which implicitly limits the number of generations in a run of the IGA and favors testing procedures that do not allow the recipient the option of reviewing or comparing members of the current generation.

Finally, from the standpoint of stimulus variation, humans are much more likely to handle heavier memory and task loads if the artefacts they are evaluating have a sufficient degree of variability. This less-formalized concept in psychometrics respects the differences in performance observed, for example, when running fixed-level vs. adaptive psychophysical methods. Fixed-level methods, in which the same stimulus condition is repeated for 50-100 trials, may suffer from lags in attention, either because the discrimination or detection task is too difficult (performance is near chance) or because it is too easy (performance is nearly perfect).

In contrast, sequential adaptive estimation methods, are better able to sustain the recipient's attention over 50-100 trials by varying the stimulus condition from trial to trial. This desire for a procedure with a sufficient degree of stimulus variation runs counter to the desire for homogeneity within a current generation as an IGA-run evolves. Stimulus variation also is known to be important in "teaching" the recipient to discriminate among those properties of the stimulus which are relevant to the task from those which are not. Accordingly, as the population homogenizes over an IGA run, recipient's are more likely to attend to those stimulus properties that make the scoring task manageable, rather than those that are indicative of potentially better variations. This is particularly a problem when the participant may not really know, at the outset of a run, what stimulus properties they prefer and only learn these from the generated exemplars.

Whereas the three factors above reflect the insertion of the human in the "feedback loop" of a genetic algorithm, psychometric theory also points to the inherent limitations of how data generated by the measurements themselves can be interpreted. In any sensory scaling task, the experimenter decides whether the data should be treated on a categorical, ordinal, interval or ratio scale. In general, without additional assumptions or more elaborate psychometric procedures, it is recognized that preference scores provided by a human recipient are no stronger than ordinal. Should the rules of parent selection assume the figure of merit to be drawn from interval or ratio scales (as is typically the case in standard genetic algorithms), then the rules should be adjusted to accommodate the weaker ordinal or even categorical nature of the data the recipient provides.

The consequences of the psychophysical limitations to the implementation of an IGA are that smaller, as opposed to larger, search spaces are likely to yield valid results, and mechanics of the selection, cross-over, and mutation processes should be scrutinized to ensure that subjects provide reliable data that is uncontaminated by fatigue, inattentiveness, and bias. Given the need for small search spaces over which to search in an IAGA, the mapping of designs to genetic representation takes on greater significance than is typically the case for a standard genetic algorithm. Binary representations may inflate the size of the search space and, as such, certain embodiments may use more efficient M-length strings such as:

$$\alpha \in A_1 \times A_2 \times \ldots \times A_M$$

where each $A_k$ is a finite alphabet of size $N_k$ and M typically corresponds to the number of sound tokens to be presented.

The best psychometric methods are those that make the most from the fewest number of observations. Applying this principle to the IAGA, duplicates within a generation are deemed wasteful observations, despite the fact that increasing homogeneity is a desired outcome of an IGA run. The IAGA modifies the standard form of generational updating through culling, tagging, and selective insertion. The process of culling removes duplicates from the next generation. Each member that remains is tagged with the number of copies that were removed. In place of the duplicates, unique members are inserted into the generation. The rules for such insertion are variable. In certain embodiments, new members (sound tokens) can be drawn from regions of the search space that haven't yet been explored, while members that have already been rejected in previous generations may be ruled out (e.g., through a tabu list).

A tabu list is a list of undesirable sound tokens (i.e., sound tokens that have been correctly identified by the recipient). That is, a running tabu list may be stored where unfit sound tokens are added to the tabu list as they are identified. The tabu list may be used to prune the global population of the search such that tabu sound tokens are removed from the global population and not included in subsequent phases of the training.

It may be possible that a recipient correctly identifies a sound token through error or accident such that he/she still has difficulty perceiving the sound token. As such, in certain embodiments, a sound token is added to the tabu list only after the recipient has correctly identified the sound token more than once (i.e., two or more times). The tabu list may persist throughout the duration of an evolution (i.e., until the end of a specific auditory training session), for a limited number of generations, or over multiple evolutions.

An often-reported comment from participants in IGA experiments is that at the beginning of a run, it is hard for them to accept any option, but as the run persists, it is even harder for them to evaluate among the very small differences of a nearly homogeneous population. Culling and selective insertion are intended to mitigate the task difficulty encountered in later generations of a run, whereas variable acceptance is intended to help with task difficulty at the beginning of a run. In a standard IGA, a certain number of parents are necessary to avoid pre-mature convergence of the population. However, the IAGA instructs the participant to accept as many, or as few, of the members of the current generation as appropriate (i.e., the IAGA does not require a set generation size).

At the most general level, the purpose of cross-over is to perpetuate schema in the search space with positive value and to eliminate all others. Mutation's role is to improve existing schema by introducing new variations in to the population. Culling and selective insertion (to the extent non-visited portions of the search space have very different schema) are counter-productive to schema formation, whereas variable acceptance is likely to reinforce larger schema to the detriment of smaller ones during the initial phase of an IAGA run.

A natural way to incorporate binary selections (of arbitrary number) with tagging (which preserves the relative dominance of a particular string within the current generation) into the cross-over operator is to generate the set of all possible children and sample without replacement from the set. Specially, it is assumed that $A=\{\alpha_1, \alpha_2, \ldots, \alpha_k\}$ is the set of accepted members from the current generation. The parents (P) are formed from A by augmenting A with each member's collection of duplicates such that $$P=\{\alpha_{1,1},\ldots,\alpha_1,N_1,\alpha_{2,1},\ldots,\alpha_2,N_2,\ldots,\alpha_{k,1},\ldots,\alpha_k,N_k\}$$

The population of potential children (C) is formed by crossing, in all possible ways, each pair of parents drawn from P. Without replacement, the proper number of strings is drawn to form the next generation. These strings may undergo mutation and then are subject to the culling, tagging, and selective insertion operators. Although the complexity of the proposed cross-over operation is larger than most cross-over operators in standard genetic algorithms, the number of computations required remains relatively small in practice owing to the fact that the size of the search space is small. In one example, a single-cut crossover for is employed for search spaces on the order of 2000, such that the computation time is negligible when compared with the time it takes for the recipient to make his/her judgments.

Initialization of IGAs is subject to the same issues encountered with a standard genetic algorithm. However, whereas standard genetic algorithms work around the problems of initialization by repeated measures, IGAs, in practice, cannot rely on more than a handful of runs. The IAGA utilizes selective insertion to introduce genetic materials into the population that may not have been encountered as well as an initialization procedure in which values of each parameter are as distinct across the population as possible.

Both variable acceptance and the culling/tagging operators complicate the application of standard rules for terminating an IGA run. It has been found that measures of genetic drift, when applied to the population of potential children during crossover, are useful indicators.

In summary, the IAGA modifies elements of an IGA which may be compromised by the psychometric limitations of the assessment procedure. The IAGA designed to efficiently utilize the recipient's time, promote their attentiveness, minimize their fatigue, and work around their bias. The use of culling, tagging, selective insertion, and variable acceptance to achieve these design goals involves a substantial reworking of cross-over, mutation, initialization, and stopping criteria in an IGA or a traditional genetic algorithm. Further details of an example IAGA are provided in Lineaweaver et al., Psychometric Augmentation of an Interactive Genetic Algorithm for Optimizing Cochlear Implant Programs, Proceedings of the 13th Annual Conference on Genetic and Evolutionary Computation 2011, pages 1755-1762, published by Association for Computing Machinery (ACM), which is hereby incorporated by reference herein.

Embodiments have been described above with reference to the use of an IAGA during the auditory training process. However, it is to be appreciated that the other genetic algorithms (e.g., a traditional genetic algorithm or an IGA) may be used during an auditory training process in accordance with alternative embodiments of the present invention. Aspects of other genetic algorithms that may be used in accordance with examples presented herein are described in commonly owned U.S. Pat. Nos. 6,879,860 and 8,301,259 and commonly owned and co-pending U.S. Patent Publication Nos. 2010/0152813, 2010/0280307, 2011/0060383, and 2011/0060702. The content of each of these documents are hereby incorporated by reference herein.

Figure 5:
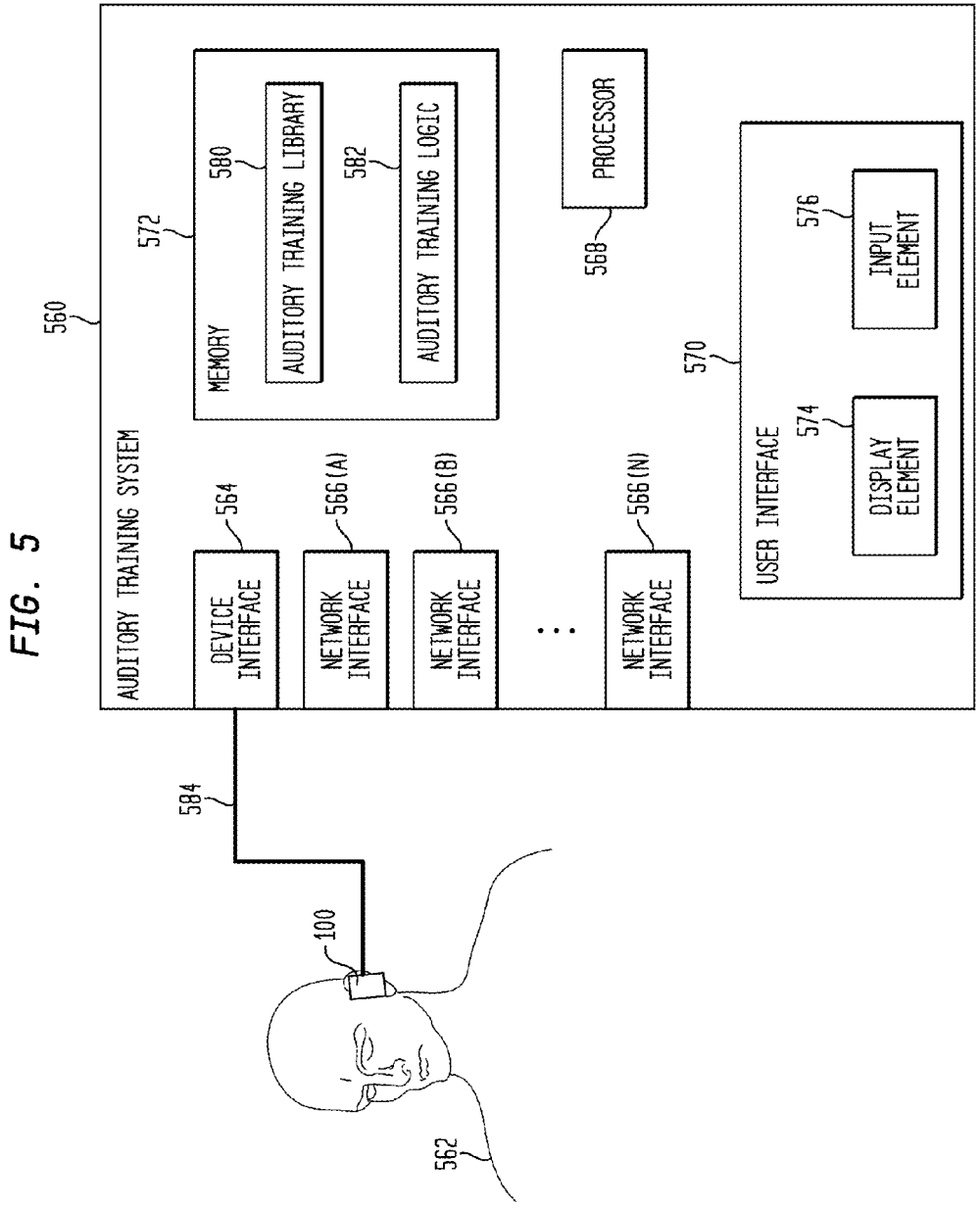
FIG. 5 is a block diagram of an auditory training system in accordance with embodiments of the present invention.

FIG. 5 is a block diagram illustrating one exemplary auditory training system 560 that may be used during auditory training of a recipient 562 of a cochlear implant 100 (FIG. 1). In the embodiments of FIG. 5, training system 560 comprises a device interface 564, a plurality of network interfaces 566(A)-566(N), a processor 568, a user interface 570, and a memory 572. User interface 570 comprises a display element 574 and an input element 576, while memory 572 comprises an auditory training library 580 and auditory training logic 582. Training system 560 may be any type of device capable of executing instructions such as, for example, a general or special purpose computer (e.g., laptop, desktop, tablet), a mobile device (e.g., personal digital assistant (PDA) or mobile phone), remote control, etc.

In the embodiment illustrated in FIG. 5, training system 560 is configured to communicate with cochlear implant 100 via device interface 564. That is, device interface 564 is configured to establish a data communication link 584 with an interface of cochlear implant 100. Device interface 564 may comprise, for example, a Universal Serial Bus (USB) interface, an Institute of Electrical and Electronics Engineers (IEEE) 1394 High Speed Serial Bus (e.g., Firewire) interface, Bluetooth, fixed line, wireless interface, or other type of interface.

Training system 560 also comprises a plurality of network interfaces 566(A)-566(N). Network interfaces 566(A)-566(N) may comprise, for example, Ethernet interfaces, Wi-Fi interfaces, 3rd generation (3G) mobile telecommunications interface, IEEE 802.11 interfaces, IEEE 802.16 (WiMAX) interfaces, Bluetooth interfaces, fixed line interfaces, Long Term Evolution (LTE) interfaces, etc. It is to be that these various interfaces may be used in any combination or a single interface may be provided. Other types of interfaces could also be used in alternative embodiments.

User interface 570 comprises a display element 574 and an input element 576. Display element 574 may be any type of display device, such as, for example, those commonly used with computer systems. Input element 576 may be any type of interface capable of receiving information from a recipient, such as, for example, a computer keyboard, mouse, voice-responsive software, touch-screen (e.g., integrated with display element 574), retinal control, joystick, and any other data entry or data presentation formats now known or later developed.

Memory 572 may comprise read only memory (ROM), random access memory (RAM), magnetic disk storage media devices, optical storage media devices, flash memory devices, electrical, optical, or other physical/tangible memory storage devices. The processor 568 is, for example, a microprocessor or microcontroller that executes instructions for the auditory training logic 582. Thus, in general, the memory 572 may comprise one or more tangible (non-transitory) computer readable storage media (e.g., a memory device) encoded with software comprising computer executable instructions and when the software is executed (by the processor 568) it is operable to perform the operations described herein in connection with the auditory training process and auditory training genetic algorithm (through execution of the auditory training logic 582).

The auditory training library 580 comprises a collection of sound tokens that may be played to the recipient 562 during the auditory training process. As noted above, an auditory training library, such as library 580, may include a large number of different types of sound tokens (e.g., language sounds, parts of music, tones, etc.) The training system 560 of FIG. 5 is also configured to allow a recipient or other user (e.g., clinician, caregiver, etc.) to add sound tokens that are specific to the recipient. For example, a recipient may have several children and it is important for the recipient to learn to differentiate the voices of the children. In such embodiments, words, phrases, or other sounds spoken by each of the children may be added to the recipient's auditory training library. These recipient-specific sound tokens may be incorporated into the sound training process so that the recipient can learn to separately identify the different children.

In certain embodiments, the ability to differentiate between children, spouses, co-workers, etc. may be of first importance to the recipient. As such, all or a certain number of the recipient-specific sound tokens may be selected for the initial generation. In the same or other embodiments, the recipient-specific sound tokens (particularly those that are incorrectly identified by the recipient) may be tagged so that there is a greater likelihood these sounds will appear in the training process.

Recipient-specific sounds may be added to the auditory training library 580 in a number of different manners. For example, the training system 560 may include a microphone or other auditory input element (not shown) that enables sound to be directly imported into the system. Alternatively, recipient-specific sounds may be recorded on another device (i.e., voice recorder, computer, etc.) and imported into the auditory training library 580 via a network interface 566(A)-566(N) or another interface.

In the embodiments of FIG. 5, sound tokens are provided to cochlear implant 100 via communication link 584 and the sound tokens are subsequently delivered to the recipient via the cochlear implant. In alternative embodiments, no communication link may be provided between cochlear implant 100 and training system 560. In such alternative embodiments, sound tokens may be played through a speaker system (not shown) that is connected to, or is a part of, training system 560. In these embodiments, the cochlear implant 100 receives and processes the sound tokens for delivery to the recipient.

FIG. 5 illustrates an example where the auditory training library 580 and auditory training logic 582 are stored and executed locally at a computing device (auditory training system 560). In other embodiments, auditory training library 580 and auditory training logic 582 may be stored and executed at a remote computing device disposed at a different location (e.g., a remote server) and are accessed through a network interface. More specifically, the one of the network interfaces 566(A)-566(N) may be configured to communicate with the remote computing device via a computing network that may comprise, for example, a local area network (LAN) or a wide area network (WAN) (e.g., the Internet).

In the same or other embodiments, the results of a genetic algorithm based auditory training process may be stored within the training system 560 and/or uploaded to a data repository (e.g., a cloud computing system via the Internet) for future use. In one example, the stored results may be used, for example, during selection of an initial generation during a subsequent auditory training process. In another example, the stored results may be (confidentially) shared with clinicians or other users to improved auditory training processes for the same or other recipients.

Figure 6A:
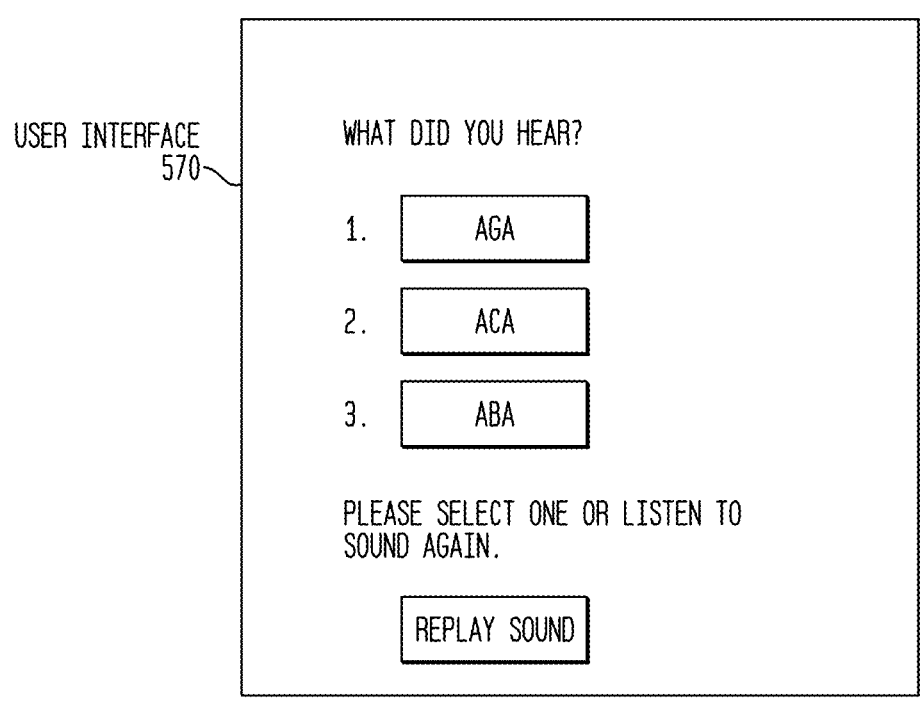

An auditory training process in accordance with embodiments of the present invention may be administered by a clinician or by the recipient at a remote location. FIGS. 6A-7B illustrative example screens that may be displayed on user interface 570 in several embodiments of the present invention. More specifically, FIG. 6A illustrates an example where a sound token corresponding to the sound "ABA" is delivered to recipient 562 via cochlear implant 100. After delivery of the sound token, the user interface 570 displays a message asking the recipient 562 to identify the sound he/she heard. In this example, a plurality of possible sounds are visually displayed at the user interface and the recipient 562 may then select one of the displayed options or choose to listen to the sound again.

Figure 6B:
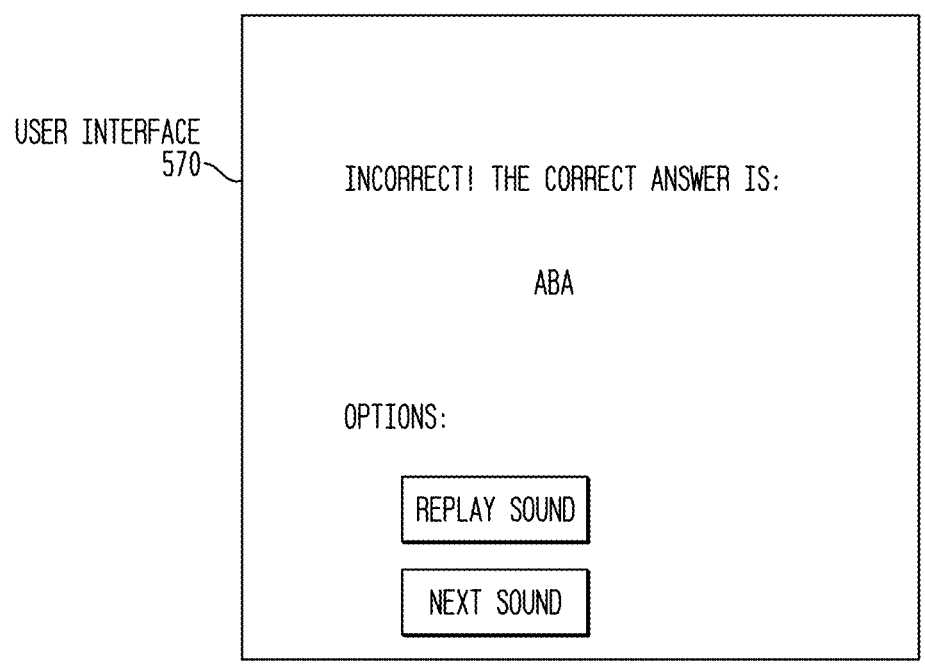

In the example of FIG. 6A, the recipient 562 makes an incorrect selection that results in the user interface 570 displaying a message as shown in FIG. 6B. Since the auditory training process is designed to improve the recipient's sound comprehension (i.e., teach the recipient 562 how to hear through the cochlear implant 100), the training system 560 illustrates the correct choice for the recipient. The training system 560 also gives the recipient 562 the option to listen to the sound again (to reinforce the lesson) or to advance to the next sound. At the time the message of FIG. 6B is displayed to the recipient 562, the training system 560 stores the played sound token as a fit sound token. That is, since the recipient 562 failed to correctly identify the sound token, the sound token is selected for use in creating the next generation of sound tokens for delivery to the recipient.

FIG. 7A illustrates an example where a sound token corresponding to first and second tones is delivered to recipient 562 via cochlear implant 100. After delivery of the sound token, the user interface 570 displays a message asking the recipient 562 to identify the sound(s) he/she heard. In this example, a plurality of possible sounds are visually displayed at the user interface and the recipient 562 may then select one of the displayed options or listen to the sound again.

Figure 7B:
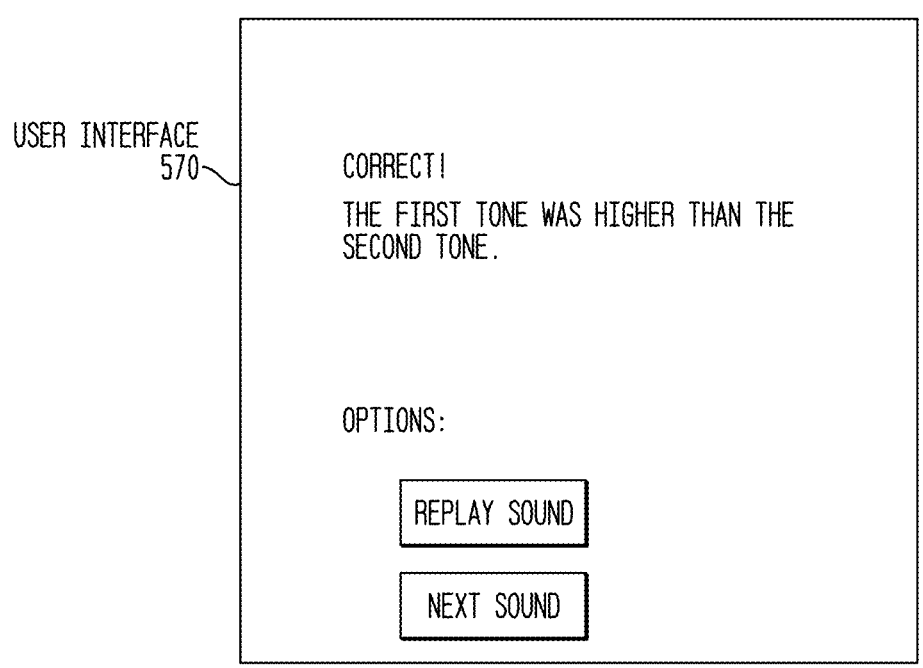

In the example of FIG. 7A, the recipient 562 correctly determines that the sound token included a first tone that was higher than a second tone, thereby resulting in the user interface 570 displaying a message as shown in FIG. 7B. Since the auditory training process is designed to improve the recipient's sound comprehension, the message notifies the recipient 562 that he/she correctly identified the sound. The training system 560 also gives the recipient 562 the option to listen to the sound again or to advance to the next sound. At the time the message of FIG. 7B is displayed to the recipient 562, the training system 560 stores the played sound token as an unfit sound token. That is, since the recipient 562 correctly identified the sound token, the sound token is not selected for use in creating the next generation of sound tokens for delivery to the recipient.

It is to be appreciated that the displays of FIGS. 6A-7B are merely illustrative and that many different types of displays and messages may be used in embodiments of the present invention. For example, alternative embodiments of the present invention may use icons corresponding to the choices that change in appearance in response to correct or incorrect selections by the recipient (e.g., chance color, shape, size, etc.).

Modern cochlear implants use a number of different operating parameters to maximize sound perception and recipient satisfaction. There are also a wide variety of fitting options that can be used to customize these various operating parameters for an individual recipient. The task of the clinical professional (e.g., clinician or audiologist) is to select a set of parameters, commonly referred to as a parameter map or, more simply a MAP, which will provide the best possible sound reception for an individual recipient. In others, when a sound is received at a cochlear implant, the recipient's MAP (i.e., selected parameters) is used to process and deliver the sound to the recipient. As such, the recipient's MAP has a profound effect on how a sound is perceived by the recipient.

Examples of parameters that are part of a recipient's MAP include, for example, the speech strategy implemented in the cochlear implant. Additionally, within any given speech strategy a great many parameters and parameter values may be specified to tailor the encoding and stimulation for an individual recipient. Examples of parameters that may be selected for a speech strategy include but are not limited to the number of channels of stimulation represented, the configuration and number of intracochlear and/or extracochlear electrodes which are to be associated with each channel, the pulse repetition rate for each channel, the pulse pattern, the width of each pulse or between pulses, the number of spectral maxima periodically chosen for representation, the mapping of sound pressure to stimulus current for each channel (threshold levels, comfort levels and compression curves), the frequency boundaries allocated for each channel, parameters for the front end filtering of the audio from the microphone (pre-emphasis), an automatic gain control threshold, channel-specific compression ratios, and attack and release times. Additional parameters may include, but are not limited to, loudness parameters such as long term loudness balance (that is, electrical and mechanical gains), parameters for short term gain manipulations, particularly signal-dependent gain adjustments. Such gain adjustment parameters include, for example, parameters for adjustments to minimize cross-modal masking, and adjustments to emphasize speech features such as noise, frication or voicing. Further parameters may include frequency domain parameters, time domain parameters, and/or binaural parameters. As one skilled in the art would appreciate, the above parameters are examples of parameters which may be selected and tailored to optimally fit a cochlear implant to a recipient.

Because there may be thousands of possible parameter maps, it is impractical for a recipient to experience all of the alternatives and to evaluate the performance of each alternative. Similarly, it is not possible to identify an optimal parameter map by prescription based on a limited set of measurements as is, for example, the case in fitting eyeglasses. Because parameters of cochlear implant systems often interact non-linearly and non-monotonically, it is also not possible to sequentially optimize parameters one at a time, adjusting each in succession to its optimal value.

In order for a recipient to hear sounds through the cochlear implant (and to be able to participate in the auditory training process described above) the recipient must receive a MAP that is used to deliver the sound tokens to the recipient. The process of selecting a recipient's MAP is often referred to as "fitting" and there are a variety of approaches for fitting the cochlear implant systems to a recipient. In one embodiment, a clinician may simply set the parameters of the MAP to default values regardless of the individual recipient. In another embodiment, preferred MAPs which have been experimentally determined to be generally good, if not best, for many or most recipients may be selected. Such preferred MAPs may be based on personal experience, published performance data, or intuition. Some clinicians evaluate a limited set of alternatives adjusting individual parameters based upon measured perceptual limitations and inferred relationships among the parameters.

In certain embodiments, a genetic algorithm may be used to select the recipient's MAP for use during the auditory training process. The use of a genetic algorithm to select a recipient's MAP is described in commonly owned U.S. Pat. Nos. 6,879,860 and 8,301,259 and commonly owned and co-pending U.S. Patent Publication Nos. 2010/0152813, 2010/0280307, 2011/0060383, and 2011/0060702. The content of each of these documents are hereby incorporated by reference herein.

In the above described embodiments, the recipient's parameter values (i.e., MAP) remain fixed so that the MAP parameters do not change during the auditory training process. As such, the recipient's hearing perception with the pre-selected parameter values (i.e., the selected MAP) improves over the course of the auditory training process. That is, the auditory training process teaches the recipient's brain to best use the MAP that was selected during the earlier fitting process.

In certain embodiments of the present invention, it may be discovered during the auditory training process described above that the recipient's current MAP is not well suited for the recipient or that the MAP needs some adjustment. In such embodiments, another fitting process may be implemented wherein the recipient's MAP is changed or refined.

Figure 8:
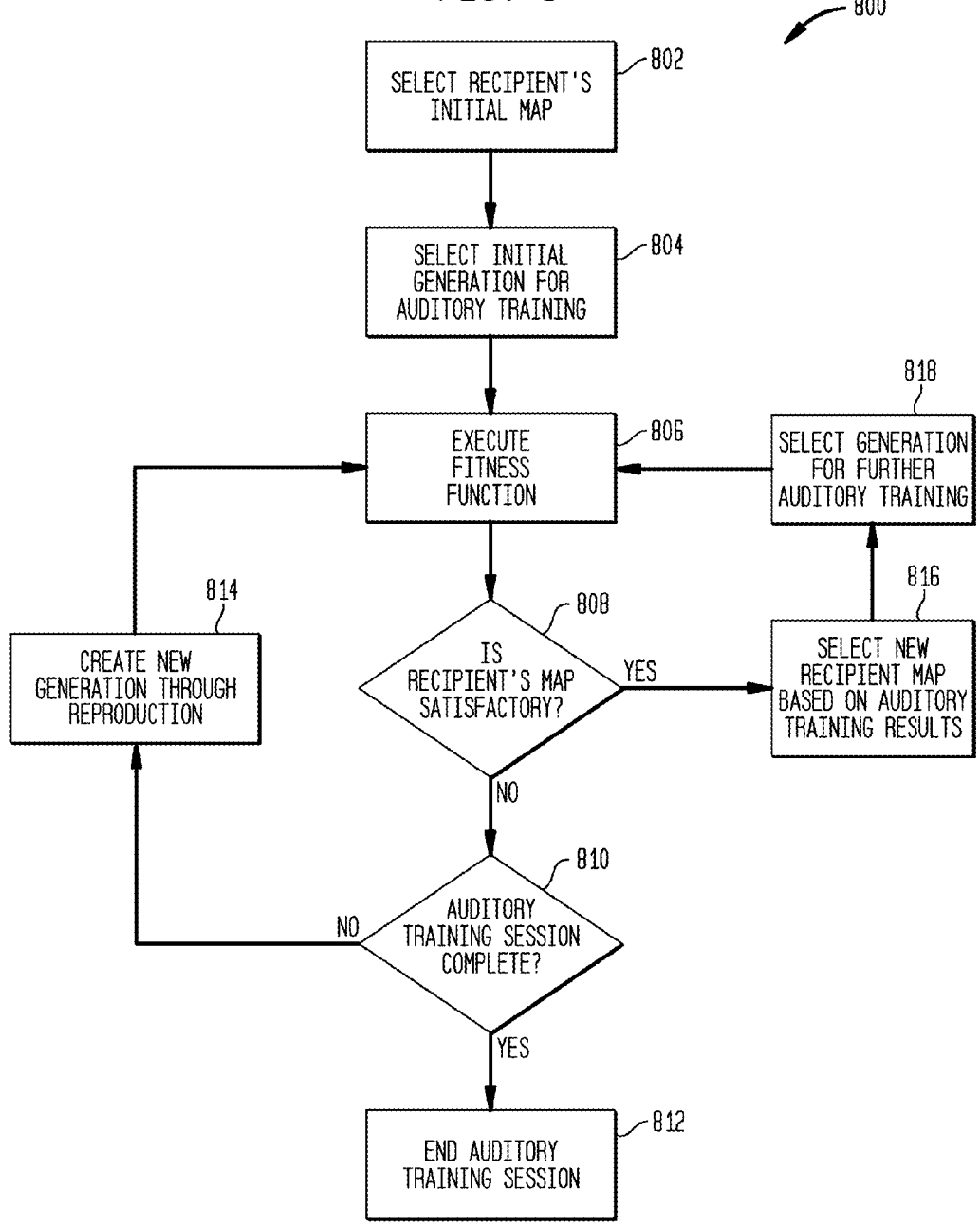
FIG. 8 is a flowchart of a method in accordance with embodiments of the present invention.

FIG. 8 is a flowchart of a method 800 in accordance with embodiments of the present invention. Method 800 begins at block 802 where a recipient's initial MAP is set or selected using, for example, a genetic algorithm based fitting process. At block 804, an initial generation of sound tokens is selected for use in an auditory training process. The selection of this initial generation may be performed in a number of different manners as described elsewhere herein. For example, the initial sound tokens may be selected at random from an auditory training library, the initial sound tokens may be selected from only a subset if the auditory training library, the initial sound tokens may be selected by an audiologist/clinician based on experience, suggestions and recommendations from others, etc.

Next, at block 806 a fitness function is executed to evaluate the initial generation. That is, the initial sound tokens are sequentially played to the recipient through the cochlear implant (e.g., via a dedicated connection or indirectly over speakers). As described above, after each sound token is played the recipient is asked to identify the sound token. In one embodiment, the auditory training is performed by, or in the presence of, a clinician and the clinician receives the recipient's identification of the sound token. The clinician may provide the recipient with several visual choices (e.g., in a book, on a screen of a computing device, etc.) and the recipient is instructed to select which possible choice is closest to the sound that he/she perceived. In another embodiment, the auditory training is performed by the recipient on a computing device at a remote location (i.e., outside of a clinician's office). In such embodiments, the computing device is configured to visually display several choices and the user selects which possible choice is closest to the sound that he/she perceived.

After execution of the fitness function for all or a selected number of sound tokens in the initial generation, a determination is made at block 808 as to whether the recipient's MAP is satisfactory. For example, if the user is unable to correctly identify a certain number (e.g., a majority) of the sound tokens, it may be determined that the recipient's initial MAP is unsatisfactory and not well-suited for the recipient.

It is to be appreciated that a number of different methods may be used to determine if a MAP is unsatisfactory. For example, the failure of a recipient to identify certain sounds may indicate MAP problems. In one embodiment, such sounds may be added to the library as markers and a failure to identify one or more of these sounds may be viewed as an indication that there is a MAP problem.

If it is determined that the recipient's MAP is satisfactory, then a second determination is made at block 810 as to whether the genetic algorithm (and the auditory training) should be stopped (i.e., whether stopping criteria have been satisfied). In one embodiment, the auditory training is stopped after a predetermined number of generations. In another embodiment, the auditory training is stopped after a predetermined period of time.

If the stopping criteria have been satisfied, then auditory training ends at block 812. Otherwise, at block 814, a new generation is created through reproduction as described elsewhere herein. The reproduction occurs using only those sound tokens that the recipient failed to correctly identify. After creation of the new generation, the fitness function is executed at block 806 on the new generation.

Returning to block 808, if it is determined that the recipient's MAP is unsatisfactory, then at block 816 a new MAP is selected for the recipient. In this embodiment, a genetic algorithm based fitting process is used to select the recipient's new MAP. In certain embodiments, the genetic algorithm based fitting process uses the auditory training results in the selection of the new MAP.

After selection of the recipient's new MAP, at block 818 a new generation of sound tokens is selected for further auditory training. In one embodiment, this new generation comprises the initial generation that was previously delivered to the recipient.

After creation of the new generation, the fitness function is executed again at block 806. The above process continues until satisfaction of the stopping criteria and/or the recipient's MAP is deemed to be satisfactory.

Cochlear implant fitting and auditory training processes may be time consuming and difficult for a recipient. As such, method 800 described above with reference to FIG. 8 may be performed over a number of different sessions.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An auditory training system, comprising:
a user interface; and
a processor configured to:
present an initial set of auditory training sound tokens to a recipient of a hearing prosthesis;
receive recipient feedback in response to presented sound tokens from the initial set of auditory training sound tokens, wherein the feedback indicates the recipient's perception of the presented sound tokens; and
execute an interactive augmented genetic algorithm to automatically increase the difficulty of the auditory training based on the recipient's perception of the presented sound tokens to create a second set of auditory sound tokens for presentation to the recipient.

2. The system of claim 1, further comprising:
a memory comprising an auditory training library,
wherein the processor is configured to select the initial set of auditory training sound tokens from the auditory training library.

3. The method of claim 1, wherein the auditory training library comprises recipient-specific sound tokens added to the auditory training library by a user.

4. The system of claim 1, wherein the processor is configured to:
sequentially present the initial set of auditory training sound tokens to the recipient via the hearing prosthesis; and
receive recipient feedback after each sequentially presented sound token.

5. The system of claim 4, wherein each sound token in the initial set of auditory training sound tokens corresponds to a known sound, and wherein to receive recipient feedback in response to a first presented sound token the processor is configured to:
receive an indication of whether the recipient correctly perceived the known sound corresponding to the first presented sound token.

6. The system of claim 5, wherein if the recipient correctly perceived the known sound corresponding to the first presented sound token, the processor is configured to add the first presented sound token to a tabu list.

7. The system of claim 6, wherein the processor is configured to:
present a visual representation of a plurality of sounds to the recipient in relation to presentation of a selected sound token;
present a request for the recipient to select one of the visual representations that corresponds to the selected sound token; and
receive a selection from the recipient of one of the visual representations.

8. One or more non-transitory computer readable storage media encoded with software comprising computer executable instructions and when the software is executed operable to:
control a hearing prosthesis to sequentially present, during auditory training, an initial set of auditory training sound tokens to a recipient of the hearing prosthesis;
receive, from a user interface, recipient feedback in response to presented sound tokens from the initiate set of auditory training sound tokens, wherein the feedback indicates whether the recipient correctly perceived known sounds corresponding to each the presented sound tokens; and
execute a genetic algorithm to automatically increase the difficulty of the auditory training based on the recipient feedback to create a second set of auditory sound tokens for presentation to the recipient.

9. The non-transitory computer readable storage media of claim 8, wherein each sound token in the initial set of auditory training sound tokens corresponds to a known sound, and wherein the instructions operable to receive recipient feedback in response to a first presented sound token comprise instructions operable to:
receive, from the user interface, an indication of whether the recipient correctly perceived the known sound corresponding to the first presented sound token.

10. The non-transitory computer readable storage media of claim 8, wherein the instructions operable to execute the genetic algorithm to automatically increase the difficulty of the auditory training based on the recipient's perception of the sound tokens comprise instructions operable to:
execute the genetic algorithm to progressively remove perceivable sounds from the auditory training so as to generate one or more sets of auditory training sound tokens that are difficult for the recipient to perceive.

11. The non-transitory computer readable storage media of claim 10, further comprising instructions operable to:

present a visual representation of a plurality of sounds to the recipient in relation to presentation of a selected sound token;

present a request for the recipient to select one of the visual representations that corresponds to the selected sound token; and receive a selection from the recipient of one of the visual representations.

12. The non-transitory computer readable storage media of claim 8, wherein the instructions operable to select the initial set of auditory training sound tokens from the auditory training library comprise instructions operable to:

select recipient-specific sound tokens added to the auditory training library by a user.

13. A method comprising:

selecting a set of parameter values for use by a cochlear implant;

providing the set of parameter values to the cochlear implant;

causing the cochlear implant to process a first set of auditory training sound tokens using the set of parameter values to generate stimulation signals for delivery to a recipient; and executing a genetic algorithm based auditory training process in which the first set of auditory training sound tokens is adjusted to create a second set of auditory sound tokens for presentation to the recipient, wherein the second set of auditory sound tokens are configured to be relatively more difficult for the recipient to perceive than the first set of auditory training sound tokens.

14. The method of claim 13, wherein selecting the set of parameter values for the cochlear implant comprises:

executing a genetic algorithm based fitting process to select the parameter values.

15. The method of claim 13, wherein executing the genetic algorithm based auditory training process comprises:

selecting the first set of auditory training sound tokens from an auditory training library;

receiving recipient feedback, wherein the feedback indicates the recipient's perception of the stimulation signals generated based on the sound tokens.

16. The method of claim 15, further comprising:

sequentially presenting the first set of sound tokens to the recipient via the cochlear implant; and receiving recipient feedback in response to the presented sound tokens after each sequentially presented sound token.

17. The method of claim 16, wherein each sound token corresponds to a known sound, and wherein the method further comprises:

in response to a first presented sound token, receiving recipient feedback comprising an indication of whether the recipient correctly perceived a known sound corresponding to the first presented sound token.

18. The method of claim 17, further comprising:

if the recipient correctly perceived the known sound corresponding to the first presented sound token, eliminating the first presented sound token for use in creation of the second set of auditory sound tokens.

19. The method of claim 13, further comprising:

during the genetic algorithm based auditory training process, determining that the selected set of parameter values for the cochlear implant is unsatisfactory.

20. The method of claim 19, further comprising:

selecting a new set of parameter values for the cochlear implant based on results from the genetic algorithm based auditory training process.

\* \* \* \* \*